(12) United States Patent
Cameron et al.

(10) Patent No.: US 6,849,374 B2
(45) Date of Patent: Feb. 1, 2005

(54) PHOTOACID GENERATORS AND PHOTORESISTS COMPRISING SAME

(75) Inventors: James F. Cameron, Cambridge, MA (US); Thomas M. Zydowsky, Worcester, MA (US)

(73) Assignee: Shipley Company, L.L.C., Marlborough, MA (US)

(*) Notice: Subject to any disclaimer, the term of this patent is extended or adjusted under 35 U.S.C. 154(b) by 0 days.

(21) Appl. No.: 10/007,855

(22) Filed: Nov. 3, 2001

(65) Prior Publication Data

US 2003/0027061 A1 Feb. 6, 2003

Related U.S. Application Data

(60) Provisional application No. 60/245,848, filed on Nov. 3, 2000.

(51) Int. Cl.$^7$ .......................... G03F 7/038; G03F 7/039; G03F 7/26; G03F 7/30
(52) U.S. Cl. ...................... 430/270.1; 430/18; 430/914; 430/921; 562/113
(58) Field of Search ................ 430/270.1, 18, 430/914, 921; 562/113

(56) References Cited

U.S. PATENT DOCUMENTS

| | | | |
|---|---|---|---|
| 5,296,332 A | * | 3/1994 | Sachdev et al. ......... 430/270.1 |
| 6,280,911 B1 | * | 8/2001 | Trefonas, III ............... 430/326 |
| 6,358,665 B1 | * | 3/2002 | Pawlowski et al. ...... 430/270.1 |

FOREIGN PATENT DOCUMENTS

| | | | | |
|---|---|---|---|---|
| DE | 295 421 A | | 10/1991 | |
| EP | 0 693 468 | | 1/1996 | |
| EP | 1 033 624 | | 9/2000 | |
| EP | 1199603 A1 | * | 4/2002 | ........... G03F/7/004 |

* cited by examiner

*Primary Examiner*—Yvette C. Thornton
(74) *Attorney, Agent, or Firm*—Peter F. Corless; Darryl P. Frickey; Edwards & Angell, LLP

(57) ABSTRACT

This invention relates to new photoacid generator compounds and photoresist compositions that comprise such compounds. In particular, the invention relates to photoacid generator compounds that generate an α,α-difluoroalkyl sulfonic acid upon exposure to activating radiation. Positive- and negative-acting chemically amplified resists that contain such PAGs are particularly preferred. The invention also includes methods for synthesis of such PAGs and α,α-difluoroalkyl sulfonic acids.

15 Claims, No Drawings

PHOTOACID GENERATORS AND PHOTORESISTS COMPRISING SAME

"This application claims the benefit of U.S. Provisional Application(s) No(s).: 60/245,848 Nov. 3, 2000

BACKGROUND OF THE INVENTION

1. Field of the Invention

This invention relates to new photoacid generator compounds ("PAGs") and photoresist compositions that comprise such compounds. In particular, the invention relates to photoacid generator compounds that generate an α,α-difluoroalkyl sulfonic acid upon exposure to activating radiation. Positive- and negative-acting chemically amplified resists that contain such PAGs and that are imaged with short wavelength radiation such as sub-300 nm and sub-200 nm radiation are particularly preferred.

2. Background

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating. The use of photoresists is generally described, for example, by Deforest, Photoresist Materials and Processes, McGraw Hill Book Company, New York (1975), and by Moreau, Semiconductor Lithography, Principals, Practices and Materials, Plenum Press, New York (1988).

Known photoresists can provide features having resolution and size sufficient for many existing commercial applications. However for many other applications, the need exists for new photoresists that can provide highly resolved images of submicron dimension.

Various, attempts have been made to alter the make-up of photoresist compositions to improve performance of functional properties. Among other things, a variety of photoactive compounds have been reported for use in photoresist compositions. See, e.g., U.S. Pat. No. 4,450,360 and European Application 615163.

More recently, certain "chemically amplified" photoresist compositions have been reported. Such photoresists may be negative-acting or positive-acting and rely on multiple crosslinking events (in the case of a negative-acting resist) or deprotection reactions (in the case of a positive-acting resist) per unit of photogenerated acid. In other words, the photogenerated acid acts catalytically. In the case of positive chemically amplified resists, certain cationic photoinitiators have been used to induce cleavage of certain "blocking" groups pendant from a photoresist binder, or cleavage of certain groups that comprise a photoresist binder backbone. See, for example, U.S. Pat. Nos. 5,075,199; 4,968,851; 4,883,740; 4,810,613; and 4.491,628, and Canadian Patent Application 2,001,384. Upon selective cleavage of the blocking group through exposure of a coating layer of such a resist, a polar functional group is provided, e.g., carboxyl, phenol or imide, which results in different solubility characteristics in exposed and unexposed areas of the resist coating layer.

SUMMARY OF THE INVENTION

We have now discovered novel photoacid generator compounds (PAGs) for use in either positive-acting or negative-acting photoresist compositions. In particular, photoacid generators are provided that can produce an optionally substituted α,α-difluoroalkyl sulfonic acid upon exposure to activating radiation.

An α,α-difluoroalkyl sulfonic acid as referred to herein indicates an alkyl sulfonic acid that has two fluoro atoms substituted on the carbon adjacent (i.e. α) to the sulfonic acid moiety (i.e. the group —$CF_2$—), but where the alkyl moiety is not fully substituted by fluoro at all available positions, i.e. the alkyl moiety is not a perfluoro moiety. For instance, suitable α,α-difluoroalkyl sulfonic acids include those of the formula $RCF_2SO_3H$, where R is other than fluoro such as hydrogen, optionally substituted $C_{1-18}$alkyl that is not filly substituted by fluoro or other electron-withdrawing groups such as other halo, optionally substituted aryl such as optionally substituted carbocyclic aryl particularly phenyl, naphthyl or anthracenyl, or optionally substituted heteroalicyclic or heteroaromatic preferably having 1 to 3 separate or fused rings with 1–3 hetero (N, O or S) ring members such as optionally substituted thienyl and the like.

Generally preferred α,α-difluoroalkyl sulfonic acids include those of the formula $R(CR^1R^2)CF_2SO^3H$, where R is a group of relatively large volume such as optionally substituted $C_{4-20}$alkyl and preferably is an alicyclic group such as cyclohexyl, adamantyl and the like; optionally substituted carbocyclic aryl such as optionally substituted phenyl, naphthyl or anthracenyl; or optionally substituted heteroalicyclic or heteroaromatic preferably having 1 to 3 separate or fused rings with 1–3 hetero (N, O or S) ring members such as optionally substituted thienyl and the like; and $R^1$ and $R^2$ are each independently hydrogen or a non-hydrogen substituents, and preferably $R^1$ and $R^2$ are each hydrogen.

We have found that photoresists containing a PAG of the invention can exhibit excellent lithographic results. Among other things, the photogenerated α,α-difluoroalkyl sulfonic acids are strong acids, but are not prone to phase separation or other migration that can be exhibited by perfluoro alkyl acids. Additionally, the ability to include a large volume substituent such as a carbon or hetero alicyclic or aryl group enables further engineering of a resist formulation that can favorably impact lithographic performance.

The α,α-difluoroalkyl sulfonic acid can be photogenerated from a variety of photoreactive molecules, including ionic compounds, such as an onium salt, as well as non-ionic compounds. Generally preferred PAG compounds of the invention that can generate an α,α-difluoroalkyl sulfonic acid upon photoactivation include onium compounds such as sulfonium and iodonium compounds; and sulfonate compounds such as N-oxyimidosulfonates, N-oxyiminosulfonates, phenolic sulfonates arylalkylsulfonates particularly benzylic sulfonates; disulfones; diazosulfones; α,α-methylenedisulfones, disulfonylhydrazines, and the like.

Preferred;photoacid generator compounds of the invention include those that comprise one or more substituents of cyclopentyl, cyclohexyl, optionally substituted phenyl, pentafluorophenyl, optionally substituted thienyl, optionally substituted naphthyl, optionally substituted adamantyl, or optionally substituted isobornyl, particularly where such substituent is a moiety of the photoacid generator compound that forms a sulfonate acid upon photoactivation of the compound.

Further provided are new methods for synthesis of PAGs of the invention. Preferred PAG syntheses of the invention include reaction of a carbonyl compound to provide a difluoro alkene which is then sulfonated to provide the α,α-difluoroalkyl sulfonic group.

Preferably, PAGs of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Preferred imaging wavelengths are sub-300 nm and sub-200 nm such as 248 nm, 193 nm and 157 nm. Longer wavelengths such as I-line (365 nm) also can be employed, particularly where a sensitizer is employed as an additional resist component.

Particularly preferred photoresists of the invention contain an imaging-effective amount of one or more PAGs as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an allyl acrylate, where the polymerized alkyl acrylate (which includes (meth)acrylates) units can undergo a deblocking reaction in the presence of photoacid. Exemplary alkyl acrylates (which includes (meth)acrylates) that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates (which includes (meth)acrylates) that can undergo a photoacid-induced reaction; such polymers have been described in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate (which includes (meth)acrylates) such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups, such as polymers as described in U.S. Pat. Nos. 5,929,176 and 6,090,526, incorporated herein by reference.

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. Nos. 5,843,624 and 6,048,664, incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083; European Published Applications EP01008913A1 and EP00930542A1; and U.S. pending patent application Ser. No. 09/143,462, filed Aug. 28, 1998, all incorporated herein by reference; and iii) polymers that contain polymerized anhydride units, particularly polymerized maleic anhydride and/or itaconic anhydride units, such as disclosed in European Published Application EP01008913A1 and U.S. Pat. No. 6,048,662, both incorporated herein by reference; and/or combinations of one or more resins of types i), ii) or iii), i.e. combinations of one or more of polymers that polymerized units of a non-aromatic cyclic olefin, polymers that contain alkyl acrylates (which includes (meth)acrylates); and/or polymers that contain polymerized anhydride units.

Resists of the invention also may comprise a mixture of distinct PAGs, typically a mixture of 2 or 3 different PAGs, more typically a mixture that consists of a total of 2 distinct PAGs. At least one PAG of the mixture will generate an α,α-difluoroalkyl sulfonic acid upon exposure to activating radiation, preferably a PAG compound of Formulae I, IA, II, IIA, III, IIIA, IV, IVA, V, VA, VI, VIA, VII and VIIA as disclosed herein. The other PAG(s) of the mixture also may generate an α,α-difluoroalkyl sulfonic acid, or may generate another photoacid. Photoresists that contain such PAG mixtures can exhibit even farther enhanced lithographic performance.

The invention also provide methods for forming relief images of the photoresists of the invention, including methods for forming highly resolved patterned photoresist images (e.g. a patterned line having essentially vertical sidewalls) of sub-quarter micron dimensions or less, such as sub-0.2 or sub-0. 1 micron dimensions.

The invention further provides articles of manufacture comprising substrates such as a microelectronic wafer or a flat panel display substrate having coated thereon the photoresists and relief images of the invention. Other aspects of the invention are disclosed infra.

DETAILED DESCRIPTION OF THE INVENTION

In a first aspect of the invention, iodonium PAGs are provided that can generate an α,α-difluoroalkyl sulfonic acid. The iodonium PAGs suitably may have substituents of optionally substituted $C_{1-18}$ alkyl such as t-butyl, pentyl and the like as well as cycloalkyl such as cyclohexyl, adamantyl, isobornyl and the like; optionally substituted carbocyclic aryl such as optionally substituted phenyl, naphthyl or anthracenyl; and optionally substituted heteroalicyclic or heteroaromatic preferably having 1 to 3 separate or fused rings and 1–3 hetero (N, O or S, preferably O or S) ring atoms, such as thienyl.

For many applications, particularly for short-wavelength imaging such as sub-200 nm particularly 193 nm imaging, especially preferred are iodonium salts that have an α,α-difluoroalkyl sulfonate counter anion, and one or more cation substituents of optionally substituted phenyl (including pentafluorophenyl), optionally substituted naphthyl and optionally substituted thienyl.

In particular, preferred iodonium PAGS of the invention include those of the following Formula I:

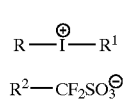

wherein R and $R^1$ are the same or different and are suitably optionally substituted alkyl (which includes carbon alicyclic); optionally substituted carbocyclic aryl; and optionally substituted heteroalicyclic or heteroaromatic (including optionally substituted thienyl); and preferably R and $R^1$ are independently optionally substituted phenyl (including pentafluorophenyl), optionally substituted naphthyl and optionally substituted thienyl; and $R^2$ is other than fluoro or other halo and is suitably hydrogen, optionally substituted $C_{1-18}$alkyl that is not fully substituted by fluoro or other electron-withdrawing groups such as other halo, optionally substituted aryl such as optionally substituted carbocyclic aryl particularly phenyl, naphthyl or anthracenyl, or optionally substituted heteroalicyclic or heteroaromatic preferably having 1 to 3 separate or fused rings with 1–3 hetero (N, O or S, preferably O or S) ring members such as optionally substituted thienyl.

Generally preferred compounds of Formula I are those where the sulfonate counter anion has a spaced "bulky" or relatively large volume substituent, such as PAGs of the following Formula IA:

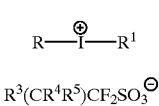

IA $R^3(CR^4R^5)CF_2SO_3^{\ominus}$ wherein R and $R^1$ are each the same as defined in Formula I above;

$R^3$ is optionally substituted alkyl having at least 4 carbon atoms, preferably optionally substituted $C_{4-20}$alkyl and preferably is an alicyclic group such as optionally substituted cyclohexyl, optionally substituted adamantyl, optionally substituted isobornyl and the like; optionally substituted carbocyclic aryl such as optionally substituted phenyl, naphthyl or anthracenyl; or optionally substituted heteroalicyclic or heteroaromatic preferably having 1 to 3 separate or fused rings with 1–3 hetero (N, O or S) ring members such as optionally substituted thienyl and the like; and $R^4$ and $R^5$ are each independently hydrogen or a non-hydrogen substituents such as optionally substituted $C_{1-20}$alkyl, optionally substituted $C_{1-20}$alkoxy, optionally substituted carbocyclic aryl such as optionally substituted phenyl; and preferably one or both of $R^4$ and $R^5$ are hydrogen.

In a further aspect of the invention, sulfonium PAGs are provided that can generate an α,α-difluoroalkyl sulfonic acid. The sulfonium PAGs suitably may have substituents of optionally substituted $C_{1-18}$ alkyl such as t-butyl, pentyl and the like as well as cycloalkyl such as cyclohexyl, adamantyl, isobornyl and the like; optionally substituted carbocyclic aryl such as optionally substituted phenyl, naphthyl or anthracenyl; and optionally substituted heteroalicyclic or heteroaromatic preferably having 1 to 3 separate or fused rings and 1–3 hetero (N, O or S, preferably O or S) ring atoms, such as thienyl.

For many applications, particularly preferred are sulfonium salts that have an α,α-difluoroalkyl sulfonate counter anion, and one or more cation substituents of optionally substituted phenyl (including pentafluorophenyl), optionally substituted naphthyl and optionally substituted thienyl.

In particular, preferred sulfonium PAGs of the invention include those of the following Formula II:

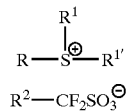

II wherein R, $R^1$ and $R^{1'}$ are the same or different and are suitably the same as defined for R and $R^1$ in Formula I above; and $R^2$ is the same as defined in Formula I.

Generally preferred compounds of Formula II are those where the sulfonate counter anion has a spaced "bulky" or relatively large volume substituent, such as PAGs of the following Formula IIA:

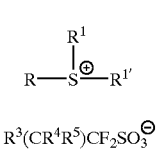

IIA wherein R, $R^1$ and $R^{1'}$ are each the same as defined in Formula II above; and $R^3$, $R^4$ and $^5$ are each the same as defined in Formula IA above.

In another aspect of the invention, optionally substituted N-oxyimidosulfonate PAGs (non-ionic compounds) are provided that have an α,α-difluoroalkyl sulfonate substituent and that can generate and an α,α-difluoroalkyl sulfonic acid upon photoactivation. In particular, preferred N-oxyimidosulfonate PAGs of the invention include those of the following Formula III:

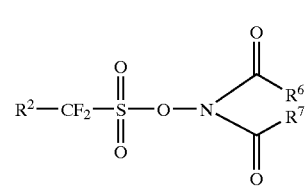

III wherein $R^2$ is other than fluoro or other halo and is suitably hydrogen, optionally substituted $C_{1-18}$alkyl that is not fully substituted by fluoro or other electron-withdrawing groups such as other halo, optionally substituted aryl such as optionally substituted carbocyclic aryl particularly phenyl, naphthyl or anthracenyl, or optionally substituted heteroalicyclic or heteroaromatic preferably having 1 to 3 separate or fused rings with 1–3 hetero (N, O or S, preferably O or S) ring members such as optionally substituted thienyl; and $R^6$ and $R^7$ are independently optionally substituted alkyl preferably having 1 to about 10 carbon atoms; optionally substituted alkoxy preferably having 1 to about 10 carbon atoms; or optionally substituted alkylthio preferably having 1 to about 10 carbon atoms, or more preferably $R^6$ and $R^7$ are taken together to form an optionally substituted alkylene or alkenylene chain preferably having 2–5 carbons so as to ring with the N and C=O groups. Such compounds can be readily prepared from open chain and cyclic N-hydroxyimides, e.g. N-hydroxysuccinimide, N-hydroxymaleimide, N-hydroxyphthalimide, N-hydroxy-1,8-naphtalimide, N-hydroxy-5-norbornene-2,3-dicarboximide, $HON(COCH_3)_2$ and the like. See also International Application WO94/10608 for preparation of N-sulfonyloxyimide PAGs.

Generally preferred PAGs of Formula III include those of the following Formula IIIA:

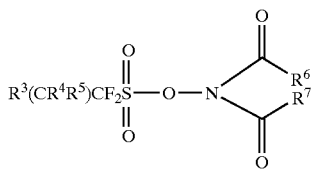

wherein $R^3$, $R^4$ and $R^5$ are each the same as defined in Formula IA above; and $R^6$ and $R^7$ are the same as defined in Formula III above.

In yet a further aspect of the invention, optionally substituted N-oxyimino sulfonate PAGs are provided that have an α,α-difluoroalkyl sulfonate substituent and that can generate and an α,α-difluoroalkyl sulfonic acid upon photoactivation. In particular, preferred N-oxyiminosulfonate PAGs of the invention include those of the following Formula IV:

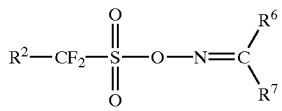

$R^2$, $R^6$ and $R^7$ are the same as defined in Formula III above. Such compounds can be readily prepared from oximes of open chain and cyclic ketones such as cyclohexanone, α-tetralone, pentanone, etc.

Generally preferred PAGs of Formula IV include those of the following Formula IVA:

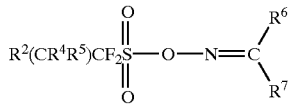

wherein $R^3$, $R^4$ and $R^5$ are each the same as defined in Formula IA above; and $R^6$ and $R^7$ are the same as defined in Formula IV above.

One preferred group of N-oxyiminosulfonate PAGs are α-cyano compounds, such as those of the following Formula V:

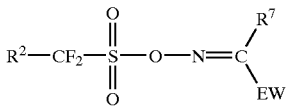

wherein $R^2$ and $R^7$ is the same as defined in Formula IV above, or $R^7$ is optionally substituted carbocyclic aryl or optionally substituted heteroaryl, particularly optionally substituted phenyl such as pentafluorophenyl, optionally substituted naphthyl or optionally substituted thienyl; and EW is an electron-withdrawing group such as cyano; haloalkyl especially halo($C_{1-8}$alkyl) such as fluoro($C_{1-8}$alkyl) preferably a perhaloalkyl such as perfluoroalkyl e.g. perfluoro($C_{1-8}$alkyl); an ester such as alkyl esters e.g. —(=O)O$C_{1-8}$alkyl and the like. Cyano is a preferred EW group. Such compounds can be prepared from open chain and cyclic acetonitrile derivatives such as 4-methoxybenzeneacetonitrile ($CH_3OC_6H_4CH_2CN$) and 1-cyclohexenylacetonitrile.

Preferred compounds of Formula V include those of the following Formula VA:

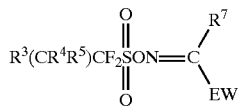

wherein $R^3$, $R^4$, $R^5$ and $R^7$ are the same as defined in Formula IVA above or $R^7$ is optionally substituted carbocyclic aryl or optionally substituted heteroaryl, particularly optionally substituted phenyl such as pentafluorophenyl, optionally substituted naphthyl or optionally substituted thienyl; and EW is the same as defined in Formula V above, with CN being a preferred EW group.

In a further aspect of the invention, optionally substituted phenolic sulfonate PAGs are provided that have one or more α,α-difluoroalkyl sulfonate substituents and that can generate and an α,α-difluoroalkyl sulfonic acid upon photoactivation. Such compounds have α,α-difluoroalkyl sulfonate groups grafted onto one or more phenolic —OH moieties, preferably two or three α,α-difuoroalkyl sufonate groups on a single phenyl group. Preferred phenolic α,α-difluoroalkyl sulfonate compounds include PAGs of the following Formula VI:

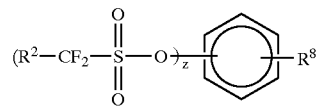

wherein $R^2$ is the same as defined in Formula I above;

$R^8$ is a non-hydrogen substituent such as halo; hydroxy; nitro; cyano; sulfonyl; optionally substituted aminoalkyl preferably having from 1 to about 20 carbon atoms, more preferably 1 to about 8 carbon atoms; optionally substituted alkoxy preferably having from 1 to about 20 carbon atoms, more preferably 1 to about 8 carbon atoms; optionally substituted aminoalkyl preferably having from 1 to about 20 carbon atoms, more preferably 1 to about 8 carbon atoms; optionally substituted alkylthio preferably having from 1 to about 20 carbon atoms, more preferably 1 to about 8 carbon atoms; optionally substituted alkylsulfinyl preferably having from 1 to about 20 carbon atoms, more preferably 1 to about 8 carbon atoms; optionally substituted alkylsulfonyl preferably having from 1 to about 20 carbon atoms, more preferably 1 to about 8 carbon atoms; optionally substituted aryloxy such as phenoxy; optionally substituted aralkyl such as benzyl; optionally substituted alkanoyl preferably having from 1 to about 20 carbons atoms with acetyl being a preferred group; optionally substituted carbocyclic aryl such as phenyl, naphthyl, biphenyl, and the like; optionally substituted heteroaromatic or heteroalicyclic having 1 to 3 rings, 3 to 8 ring members in each ring and from 1 to 3 hetero atoms such as thienyl;

m is an integer from 0 (i.e. no $R^8$ groups) to 4;

z is an integer from 1 to 6, and z is preferably is 1, 2, 3 or 4, and the sum of m and z does not exceed 6.

Preferred compounds of Formula VI include those of the following Formula VIA:

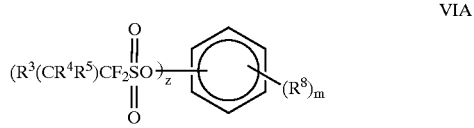

VIA wherein $R^3$, $R^4$ and $R^5$ are the same as defined in Formula VA above; and $R^8$, z and m are the same as defied in Formula VI above.

Compounds of Formulae VI and VIA can be readily prepared, e.g. by reaction of a phenolic compound with an α,α-difluoroalkyl sulfonate reagent (e.g. α,α-difluoroalkyl sulfonyl chloride) to thereby transfer the desired α,α-difluoroalkyl moieties onto a phenolic base compound.

In a yet further aspect, optionally substituted aralkyl sulfonate PAGs are provided that have one or more α,α-difluoroalkyl sulfonate moieties. Preferred PAGs of this type are benzylic compounds. Such compounds have one or more α,α-difluoroalkyl sulfonate groups grafted onto one or more benzylic carbons, preferably one or two α,α-difluoroalkyl sulfonate groups on a single phenyl base group. Preferred benzylic α,α-difluoroalkyl sulfonate compounds include PAGs of the following Formula VII:

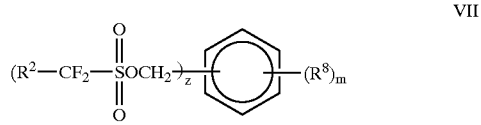

VII wherein $R^2$ is the same as defined in Formula I above; and $R^8$, m and z are the same as defined in Formula VI above.

Preferred compounds of Formula VII include those of the following Formula VIIA:

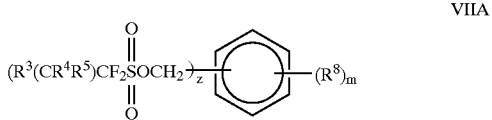

VIIA wherein $R^3$, $R^4$ and $R^5$ are the same as defined in Formula VIA above; and $R^8$, z and m are the same as defined in Formula VII above.

As mentioned above, various substituent groups of PAGs of the invention may be optionally substituted. Substituted moieties (including substituted $R^1$ through $R^8$) are suitably substituted at one or more available positions by, e.g., halogen such as F, Cl Br and/or I, alkyl including $C_{1-16}$alkyl with $C_{1-8}$alkyl being preferred, alkoxy including $C_{1-16}$ alkoxy having one or more oxygen linkages with $C_{1-8}$alkoxy being preferred, alkenyl including $C_{2-12}$alkenyl with $C_{2-8}$alkenyl being preferred, alkenyl including $C_{2-12}$alkenyl with $C_{2-8}$alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthracenyl and naphthyl.

As used herein, the term alkyl unless otherwise modified refers to both cyclic (alicyclic) and noncyclic groups, although of course cyclic groups will comprise at least three carbon ring members. Preferred alicyclic groups include e.g. cyclopentyl, cyclohexyl, and bridged groups such as adamantyl, and the like. Preferred heteroalicyclic and heteroaromatic groups of PAGs of the invention include e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazol, tetrahydrofuranyl, tetrahydropyranyl, piperdinyl, morpholino, and pyrrolindinyl.

As discussed above, novel synthetic methods are provided to produce α,α-difluoroalkyl sulfonate compounds. Preferred synthetic methods of the invention are exemplified by the following Scheme:

SCHEME

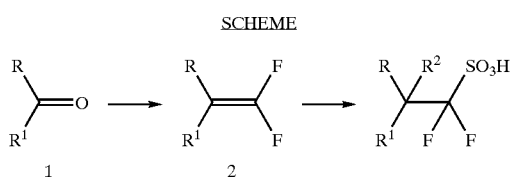

As shown in the above exemplary Scheme, a 1,1-difluoroalkene 2 is reacted with a sulfur-containing reagent preferably by a free radical mechanism to provide the α,α-difluoroalkyl sulfonate compound 3. References herein to a 1,1-difluoroalkene mean that two fluoro atoms are directly, covalently linked to a single alkene carbon, as exemplified by compound 2 above.

Preferably, the alkene carbon with difluoro substitution has a carbon-carbon double bond to a carbon that is substituted with a "bulky" substituent shown as $R^1$ in compound 2 above, such as optionally substituted $C_{4-20}$alkyl and preferably is an alicyclic group such as cyclohexyl, adamantyl and the like; optionally substituted carbocyclic aryl such as optionally substituted phenyl, naphthyl or anthracenyl; or optionally substituted heteroalicyclic or heteroaromatic preferably having 1 to 3 separate or fused rings with 1–3 hetero (N, O or S) ring members such as optionally substituted thienyl and the like. The substituent R shown in the compounds of the above Scheme is suitably hydrogen or a non-hydrogen substituent such as $C_{1-8}$alkyl, or a group as defined for $R^1$ immediately above.

The sulfur reagent that is reacted with the 1,1-difluoroalkene 2 suitably is a sulfite or bisulfite, which can provide the di-fluoro sulfonic acid 3 directly, i.e. without any active reagent. In the Scheme, the substituent $R^2$ can be the same or different than R or $R^1$. Preferably, R2 is hydrogen, and R2 may suitably be hydrogen (to provide an aldehyde) or other group such as $C_{1-8}$alkyl (to provide a ketone). Other suitable sulfur reagents include thiol acids or thiol compounds such as $H_2S$ or $CH_3C(=O)SH$, which suitably are reacted with a 1,1-difluoroalkene reagent in combination with an oxidizing agent such a peroxide e.g. hydrogen peroxide. For instance, the 1,1-difluoroalkene compound can be treated in solution with a thiol acid or thiol reagent followed by addition of the oxidizing agent to the reaction solution See Example 2 which follows for exemplary preferred reaction conditions.

The 1,1-difluoroalkene 2 can be readily prepared from a corresponding ketone (i.e. R is $C_{1-8}$alkyl or other non-hydrogen substituent) or aldehyde compound (i.e. R is hydrogen) 1 e.g. by reaction with a difluoroacetic acid in the presence of a phosphine e.g. triphenyl phosphine as generally shown in the above Scheme. The ketone compound 1, difluoroacetic acid and triphenylphosphine are suitably admixed in a suitable solvent, e.g. ethylene glycol dimethyl ether, chloroform and the like stirred for an extended period, e.g. at least about 20, 30, 50, 60, 70, or 90 hours, preferably for at an elevated temperature, e.g. at least about 40° C. or 50° C., or at reflux. See Example 1 which follows for exemplary preferred reaction conditions.

The synthesis of the invention also can be carried out as a "one-pot" procedure, i.e. in synthesis from a starting reagent of a ketone compound 1 or a 1,1-difluoroalkene compound 2 to provide difluoro sulfonic acid 3 in a single reaction vessel without isolation of any intermediate reaction products.

The formed 1,1-difluoroalkylsulfonic acid then can be reacted with a formed iodonium cation or sulfonium cation to provide an onium salt of the invention. Suitably the onium cation compound undergoes an anion exchange reaction to provide a PAG of the invention. For example, the onium compound and the 1,1-difluorosulfonic acid can be reacted in a two-phase system suitably at room temperature for an extended period, e.g. at least about 5, 10, 15 or 20 hours. See Example 3 which follows for exemplary preferred reaction conditions.

As discussed above, PAGs of the invention are useful as the radiation sensitive component in photoresist compositions, including both positive-acting and negative-acting chemically amplified resist compositions.

The photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution.

For imaging at wavelengths greater than 200 nm, such as 248 mm, phenolic resins are typically preferred. Preferred phenolic resins are poly (vinylphenols) which may be formed by block polymerization, emulsion polymerization or solution polymerization of the corresponding monomers in the presence of a catalyst. Vinylphenols useful for the production of polyvinyl phenol resins may be prepared, for example, by hydrolysis of commercially available coumarin or substituted coumarin, followed by decarboxylation of the resulting hydroxy cinnamic acids. Useful vinylphenols may also be prepared by dehydration of the corresponding hydroxy alkyl phenols or by decarboxylation of hydroxy cinnamic acids resulting from the reaction of substituted or nonsubstituted hydroxybenzaldehydes with malonic acid. Preferred polyvinylphenol resins prepared from such vinylphenols have a molecular weight range of from about 2,000 to about 60,000 daltons.

Copolymers containing phenol and nonaromatic cyclic alcohol units also are preferred resin binders for resists of the invention and may be suitably prepared by partial hydrogenation of a novolak or poly(vinylphenol) resin. Such copolymers and the use thereof in photoresist compositions are disclosed in U.S. Pat. No. 5,128,232 to Thackeray et al.

Additional suitable resins include those formed from bishydroxymethylated compounds, and block novolak resins. See U.S. Pat. Nos. 5,130,410 and 5,128,230 where such resins and use of same in photoresist compositions is disclosed. Additionally, two or more resin binders of similar or different compositions can be blended or combined together to give additive control of lithographic properties of a photoresist composition. For instance, blends of resins can be used to adjust photospeed and thermal properties and to control dissolution behavior of a resist in a developer.

Preferably, a photoacid generator compound of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

For imaging at wavelengths greater than 200 nm, such as 248 nm, a particularly preferred chemically amplified photoresist of the invention comprises in admixture a photoactive component of the invention and a resin binder that comprises a copolymer containing both phenolic and non-phenolic units. For example, one preferred group of such copolymers has acid labile groups substantially, essentially or completely only on non-phenolic units of the copolymer, particularly alkylacrylate photoacid-labile groups, i.e. a phenolic-alkyl acrylate copolymer. One especially preferred copolymer binder has repeating units x and y of the following formula:

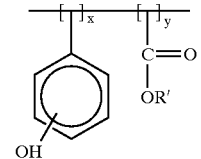

wherein the hydroxyl group be present at either the ortho, meta or para positions throughout the copolymer, and R' is substituted or unsubstituted alkyl having 1 to about 18 carbon atoms, more typically 1 to about 6 to 8 carbon atoms. Tert-butyl is a generally preferred R' group. An R' group may be optionally substituted by e.g. one or more halogen (particularly F, Cl or Br), $C_{1-8}$ alkoxy, $C_{2-8}$ alkenyl, etc. The units x and y may be regularly alternating in the copolymer, or may be randomly interspersed through the polymer. Such copolymers can be readily formed. For example, for resins of the above formula, vinyl phenols and a substituted or unsubstituted alkyl acrylate such as t-butylacrylate and the like may be condensed under free radical conditions as known in the art. The substituted ester moiety, i.e. R'—O—C(=O)—, moiety of the acrylate units serves as the acid labile groups of the resin and will undergo photoacid induced cleavage upon exposure of a coating layer of a photoresist containing the resin. Preferably the copolymer will have a $M_w$ of from about 8,000 to about 50,000, more preferably about 15,000 to about 30,000 with a molecular weight distribution of about 3 or less, more preferably a molecular weight distribution of about 2 or less. Non-phenolic resins, e.g. a copolymer of an alkyl acrylate such as t-butylacrylate or t-butylmethacrylate and a vinyl alicyclic such as a vinyl norbornanyl or vinyl cyclohexanol compound, also may be used as a resin binder in compositions of the invention. Such copolymers also may be prepared by such free radical polymerization or other known procedures and suitably will have a $M_w$ of from about 8,000 to about 50,000, and a molecular weight distribution of about 3 or less.

Another preferred resin binder for a positive chemically amplified resist of the invention has phenolic and nonaromatic cyclic alcohol units, wherein at least of portion of the hydroxyl groups of the copolymer are bonded to acid labile groups. Preferred acid labile moieties are acetate groups including t-butyl acetate groups of the formula $(CH_3)_3COC(O)CH_2$—; oxycarbonyl groups such as t-butyl oxycarbonyl (t-Boc) groups of the formula $(CH_3)_3CC(O)O$—; and acetal and ketals. Chemically amplified positive-acting photoresists containing such a copolymer have been disclosed in U.S. Pat. No. 5,258,257 to Sinta et al.

Other preferred resins that have acid-labile deblocking groups for use in a positive-acting chemically-amplified photoresist of the invention have been disclosed in European Patent Application 0829766A2 of the Shipley Company (resins with acetal and ketal resins) and European Patent Application EP0783136A2 of the Shipley Company (terpolymers and other copolymers including units of 1) styrene; 2) hydroxystyrene; and 3) acid labile groups, particularly alkyl acrylate acid labile groups such as t-butylacrylate or t-butylmethacrylate). In general, resins having a variety of acid labile groups will be suitable, such as acid sensitive esters, carbonates, ethers, imides, etc. The photoacid labile groups will more typically be pendant from a polymer backbone, although resins that have acid labile groups that are integral to the polymer backbone also may be employed.

PAGs of the invention (which includes PAGs of Formulae I, IA, II, IIA, III, IIIA, IV, IVA, V, VA, VI, VIA, VII and VIIA as defined above) also are preferably used with polymers that contain one or more photoacid-labile groups and that are substantially, essentially or completely free of phenyl or other aromatic groups. Such photoresist compositions are particularly useful for imaging with sub-200 nm radiation such as 193 nm radiation.

For example, preferred polymers contain less than about 5 mole percent aromatic groups, more preferably less than about 1 or 2 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged with such short wavelength radiation.

Suitable polymers that are substantially or completely free of aromatic groups and may be formulated with a PAG of the invention to provide a photoresist for sub-200 nm imaging are disclosed in European application EP930542A1 of the Shipley Company.

Suitable polymers that are substantially or completely free of aromatic groups suitably contain acrylate units such as photoacid-labile acrylate units as may be provided by polymerization of methyladamantylacrylate, methyladamantylmethacrylate, ethylfenchylacrylate, ethylfenchylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride; and the like.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention.

Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

Photoresists of the invention also may contain other materials. For example, other optional additives include actinic and contrast dyes, anti-striation agents, plasticizers, speed enhancers, sensitizers (e.g. for use of a PAG of the invention at longer wavelenghs such as I-line), etc. Such optional additives typically will be present in minor concentration in a photoresist composition except for fillers and dyes which may be present in relatively large concentrations such as, e.g., in amounts of from 5 to 30 percent by weight of the total weight of a resist's dry components.

A preferred optional additive of resists of the invention is an added base, particularly tetrabutylammonium hydroxide (TBAH), which can enhance resolution of a developed resist relief image. The added base is suitably used in relatively small amounts, e.g. about 1 to 10 percent by weight relative to the PAG, more typically 1 to about 5 weight percent. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; proponiates, particularly methyl propionate, ethyl propionate and ethyl ethoxy propionate; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image.

The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Printed circuit board substrates such as copper clad laminates are also suitable substrates. Substrates used for liquid crystal display and other flat panel display applications are also suitably employed, e.g. glass substrates, indium tin oxide coated substrates and the like.

A liquid coating resist composition may be applied by any standard means such as spinning, dipping or roller coating. Photoresists of the invention also may be applied as dry film resists, particularly for printed circuit board manufacture applications. The exposure energy should be sufficient to effectively activate the photoactive component of the radiation sensitive system to produce a patterned image in the resist coating layer. Suitable exposure energies typically range from about 1 to 300 mJ/cm$^2$. Suitable exposure wavelengths include sub-300 nm such as 248 nm or sub-200 nm such as 193 nm and 157 mm, or longer wavelengths such as 365 nm. Higher energy exposure sources also may be employed such as EUV, electron beam, ion beam and x-ray radiation, and other ionizing radiation. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

All documents mentioned herein are incorporated herein by reference. The following non-limiting examples are illustrative of the invention.

EXAMPLES 1–3

PAG Syntheses

Example 1

Synthesis of 1,1-difluoro-2-(1-naphthyl)ethenylene (compound 2 shown in the above Scheme where R is naphthyl).

An oven-dried 250 mL, one-neck flask was fitted with a magnetic stir bar, a reflux condenser, and a nitrogen inlet. The flask was charged with freshly distilled 1-naphthaldehyde (17.1 g, 109 mmol), chlorodifluoroacetic acid sodium salt (25 g, 164 mmol), and triphenylphosphine (31.4 g, 120 mmol). Ethylene glycol dimethyl ether (75 mL) was added and the mixture was refluxed for 96 hours during which time a precipitate formed and the reaction tuned dark brown. The cooled mixture was filtered and the filtered solution was concentrated to afford a dark semi-solid. Distillation (62–67° C., 1 mm) afforded the title compound as a colorless liquid (14.1 g, 68%). NMR (CDCl$_3$): $\delta$ 7.3–8.0 (m, 7M, 5.83 (dd, $J_1$=18 Hz), $J_2$=3 Hz); MS: M$^+$=190.

Example 2

Synthesis of 1,1-difluoro-1-sulfonic acid-2-(1-naphthyl)ethylene (compound 3 shown in the above Scheme where R is naphthyl).

A two-phase mixture of the compound of Example 1, i.e. 1,1-difluoro-2-(1-naphthyl)ethenylene (8.4 g, 44.2 mmol), sodium sulfite (28 g, 222 mmol), and benzoyl peroxide (1.1 g, 4.5 mmol) in water (200 mL) was heated for 67 hours at 85° C. The light yellow reaction mixture was filtered and the solid was suspended in tetrahydrofuran (950 mL) and the suspension was refluxed for 30 minutes. The cooled suspension was filtered and the filtrate was concentrated to afford a light tan solid. The solid was triturated with chloroform (500 mL) and the colorless solid obtained by filtration was dried to afford the desired product (2.85 g, 22%). NMR (DMSO-d$_6$): $\delta$ 7.3–8.0 (m, 7H), 5.83 (dd, $J_1$=18 Hz, $J_2$=3 Hz); MS: M$^+$=190.

Example 3

Synthesis of Di(4-tert-butylphenyl)-iodonium 1,1-difluoro-1-sulfonate-2-(1-naphthyl)ethylene (compound of Formula IA where R=R$^1$=4-t-butylphenyl; R$^3$=naphthyl; R$^4$=R$^5$=H)

A solution of the product of Example 2, i.e. 1,1-difluoro-1-sulfonic acid-2-(1-naphthyl)ethylene (8.3 g, 21.4 mmol), in dichloromethane (250 mL) was treated with a solution of di(4-tert-butylphenyl)-iodonium sulfate (9.04 g, 20 mmol) in water (150 mL). The two-phase mixture was vigorously stirred for 17 hours at room temperature, and then the pH of the aqueous phase was adjusted to 7–8 using concentrated aqueous ammonium hydroxide. The layers were separated and the organic layer was washed with water (1×200 mL). The combined aqueous extracts were extracted with dichloromethane (1×200 mL) which was then combined with the previously obtained organic phase. The combined organic extracts were concentrated to afford a tan solid. Recrystallization from benzene/hexane and then ethyl acetate/hexane afforded the desired compound as a light yellow powder (9.7 g, 73%).

Example 4

Photoresist Preparation and Lithographic Processing

A photoresist of the invention is prepared by mixing the following components with amounts expressed as weight percent based on total weight of the resist compositions:

| Resist components | Amount (wt. %) |
| --- | --- |
| Resin binder | 15 |
| Photoacid generator | 3 |
| Ethyl lactate | 81 |

The resin binder is a terpolymer consisting of polymerized vinylphenol units, styrene units and t-butylacrylate. The photoacid generator was the compound prepared in Example 3 above. Those resin and PAG components are admixed in the ethyl lactate solvent.

The formulated resist composition is spin coated onto ARC-coated six inch silicon wafers and softbaked via a vacuum hotplate at 130° C. for 60 seconds. The resist coating layer is exposed through a photomask at 248 nm, and then the exposed coating layers are post-exposure baked at 130° C. for 90 seconds. The coated wafers are then treated with 0.26N aqueous tetramethylammonium hydroxide solution to develop the imaged resist layer and provide a relief image.

The foregoing description of the invention is merely illustrative thereof, and it is understood that variations and modifications can be effected without departing from the spirit or scope of the invention as set forth in the following claims.

What is claimed is:

1. A chemically-amplified positive-acting photoresist composition comprising:
    a) a resin that comprises photoacid-labile groups; and
    b) one or more photoacid generator compounds other than a N-oxyimidosulfonate that upon exposure to activating radiation generate an acid of the formula $R(CR^1R2)CF_2SO_3H$
    where R is optionally substituted alkyl having 4 to about 20 carbon atoms, optionally substituted alicyclic group, optionally substituted carbocyclic aryl group, optionally substituted heteroalicyclic group, or optionally substituted heteroaromatic group, and R is not perhaloalkyl; and
    $R^1$ and $R^2$ are each independently hydrogen or non-hydrogen substituent.

2. The photoresist composition of claim 1 wherein R is optionally substituted alkyl.

3. The photoresist composition of claim 1 wherein R is an optionally substituted alicyclic group.

4. The photoresist composition of claim 1 wherein R is an optionally substituted carbocyclic aryl group.

5. The photoresist composition of claim 1 wherein R is an optionally substituted heteroalicyclic group, or optionally substituted heteroaromatic group.

6. The photoresist composition of claim 1 wherein the one or more photoacid generator compounds are iodonium compounds.

7. The photoresist composition of claim 1 wherein the one or more photoacid generator compounds are sulfonium compounds.

8. The photoresist of claim 1 wherein the one or more photoacid generators are non-ionic compounds.

9. The photoresist composition of claim 1 wherein one or more photoacid generator compounds are sulfonate compounds.

10. The photoresist composition of claim 1 wherein one or more photoacid generator compounds are diazosulfone compounds.

11. The photoresist composition of claim 1 wherein the resin comprises phenolic groups.

12. The photoresist composition of claim 1 wherein the resin is at least substantially free of aromatic groups.

13. The photoresist of claim 1 wherein the resin is completely free of aromatic groups.

14. An article of manufacture comprising a coating layer of a photoresist composition of claim 1.

15. The article of manufacture of claim 14 wherein the article is a microelectronic wafer substrate.

* * * * *